(12) United States Patent
Beilfuss et al.

(10) Patent No.: US 8,795,698 B2
(45) Date of Patent: Aug. 5, 2014

(54) SYSTEM CLEANER CONCENTRATE

(75) Inventors: Wolfgang Beilfuss, Hamburg (DE); Ralf Gradtke, Tornesch (DE); Ingo Krull, Kummerfeld (DE)

(73) Assignee: Air Liquide Sante (International), Paris (FR)

( * ) Notice: Subject to any disclaimer, the term of this patent is extended or adjusted under 35 U.S.C. 154(b) by 1241 days.

(21) Appl. No.: 11/830,096

(22) Filed: Jul. 30, 2007

(65) Prior Publication Data

US 2008/0027142 A1 Jan. 31, 2008

(30) Foreign Application Priority Data

Jul. 28, 2006 (DE) .......................... 10 2006 035 013

(51) Int. Cl.
*A01N 25/00* (2006.01)

(52) U.S. Cl.
USPC ........................................ 424/405

(58) Field of Classification Search
None
See application file for complete search history.

(56) References Cited

U.S. PATENT DOCUMENTS

| | | | | |
|---|---|---|---|---|
| 5,965,513 | A * | 10/1999 | Allan et al. | 510/422 |
| 6,348,483 | B1 * | 2/2002 | Beilfuss et al. | 514/374 |
| 2001/0021711 | A1 * | 9/2001 | Beilfuss et al. | 514/245 |
| 2004/0082473 | A1 * | 4/2004 | Beilfuss et al. | 504/114 |

* cited by examiner

*Primary Examiner* — Kyle Purdy
(74) *Attorney, Agent, or Firm* — Young & Thompson

(57) ABSTRACT

A concentrate for cleaning and disinfecting includes (i) one or more alkyl alcohol alkoxylates, (ii) one or more formaldehyde donor compounds, (iii) optionally one or more biocidal, in particular fungicidal, active ingredient(s), (iv) optionally one or more glycols and (v) optionally up to 10% by weight of water. Concentrates according to the invention can be formulated with a high content of formaldehyde donor compound without an undesired formaldehyde odor arising.

17 Claims, No Drawings

SYSTEM CLEANER CONCENTRATE

The present invention relates to liquid concentrates for the cleaning and disinfection of installations, equipment and pipelines, in particular in the metal working industry. The concentrates according to the invention have a high content of formaldehyde which can be cleaved off and are, inter alia, characterized in that they have a low water content or are even water-free. Moreover, the invention relates to the use of the concentrates for cleaning and disinfection, and to a corresponding dilute aqueous solution.

For cleaning and disinfecting installations in the metal working industry, use is often made of compositions which have a content of active ingredients which liberate formaldehyde (formaldehyde donor compounds). For economic and ecological reasons (formulation costs, transportation and storage costs), it is desirable to provide concentrates with a high fraction of active ingredient which are accordingly effective even at a low use concentration but have high storage stability even in concentrated form. However, a disadvantage which has been found is that concentrates with active ingredients whose mechanism of action is based on the release of formaldehyde have an intense and unpleasant pungent formaldehyde odour with increasing active ingredient content.

System cleaners are currently used which are in the form of water-containing concentrates and comprise a combination of active ingredients. Prior to use, the concentrates are diluted with water and used for the cleaning and disinfection of installations. For example, the product Grotanol® SR 3 from the applicant comprises formaldehyde donor compounds and the further active ingredients pyrione-Na and N-octylisothiazolin-3-one and consists of more than 50% by weight of water.

For cleaning and disinfection, it is recommended to use Grotanol® SR 3 in an amount of 1% by weight. More dilute aqueous solutions no longer have adequate cleaning and microbicidal effectiveness.

It has hitherto not been possible to prepare system cleaner concentrates which have a relatively high content of formaldehyde which can be cleaved off because concentrates with a relatively high active ingredient content have such an intense odour that it is unreasonable for the user. Added to this is a need for cleaners and disinfectants which do not necessarily have to comprise numerous active ingredients alongside one another and nevertheless have good microbicidal effectiveness.

Accordingly, the object of the present invention was based on providing a cleaner and disinfectant which overcomes the described disadvantages of the prior art and is advantageous in terms of odour particularly despite a high content of formaldehyde donor compound.

According to the invention, it has now surprisingly been found that this object is achieved by a concentrate for cleaning and disinfection which comprises
- (i) one or more alkyl alcohol alkoxylates,
- (ii) one or more formaldehyde donor compounds,
- (iii) optionally one or more biocidal, in particular fungicidal, active ingredient(s) chosen from pyrithione compounds, phenols and phenol derivatives, aromatic alcohols or derivatives of aromatic alcohols, isothiazolones, cyclo-hexylhydroxydiazene 1-oxide and derivatives,
- (iv) optionally one or more glycols and
- (v) optionally up to 10% by weight of water.

Compared with previously known water-rich concentrates, concentrates according to the invention are characterized in that they comprise a high fraction of formaldehyde donor compound (i.e. are low-water or even water-free) and can therefore be used in a lower use concentration as dilute aqueous solution. Nevertheless, they have a low formaldehyde odour.

(i) Alkyl Alcohol Alkoxylate

Alkyl alcohol alkoxylates used according to the invention are derived from linear or branched aliphatic alcohol having 6 to 14 carbon atoms, preferably 8 to 14 carbon atoms, which is alkoxylated with up to 20 ethylene oxide, propylene oxide and/or butylene oxide groups. Particularly preferred alkyl alcohol alkoxylates are chosen from (a) isodecyl alcohol-7 ethylene oxide, such as the commercial product Lutensol® ON 70, (b) aliphatic $C_{12}$— to $C_{18}$-alcohol ethylene oxide/butylene oxide (not terminally capped), such as Plurafac® LF 224 and (c) aliphatic $C_8$- to $C_{14}$-alcohol ethylene oxide/butylene oxide not terminally capped, such as Lutensol® LF 120.

The total amount of component (i) is in the range from 2 to 50% by weight, preferably 5 to 40% by weight, more preferably 10 to 30% by weight and in particular 15 to 25% by weight and can be provided in the form of a single alkyl alcohol alkoxylate. Mixtures of representatives of the abovementioned groups (a), (b) and/or (c) are likewise suitable.

(ii) Formaldehyde Donor Compound

Reaction products of formaldehyde and amines (preferably alkanolamines) and/or alcohols (preferably glycols and/or polyols) with a formaldehyde excess (molar ratio of formaldehyde to amine or alcohol<1:1) are particularly suitable as formaldehyde donor compounds. Examples of formaldehyde donor compounds are N-formals, such as condensation products of paraformaldehyde and isopropanolamine in the molar ratio 3:2, condensation products of paraformaldehyde and isopropanolamine in the molar ratio 3:2 and urea and condensation products of paraformaldehyde and isopropanolamine in the molar ratio 3:2, and urea and ethylene glycol. 3,3'-Methyl-enebis(5-methyloxazolidine) is particularly preferred as formaldehyde donor compound.

The amount of formaldehyde donor compound can best be quantified by stating the amount of cleavable formalde-hyde which the compound introduces into the concentrate, based on the weight of the concentrate. Preferred amounts of cleavable formaldehyde in the concentrates according to the invention are 5% by weight or more, preferably 10% by weight or more, such as 15% by weight or more or even 18% by weight or more, based on the weight of the concentrate. The amount of cleavable formaldehyde is determined experimentally using the method which is described in more detail in the examples of the present application. Preferred amounts of formaldehyde donor compounds are in the range from 2 to 50% by weight, preferably 45%, more preferably 10 to 30% by weight and in particular 15 to 25% by weight, such as for example 20% by weight, based on the weight of the concentrate.

(iii) Biocidal, in Particular Fungicidal, Active Ingredients

The one or more biocidal or fungicidal active ingredient(s) is (are) chosen from pyrithione compounds such as pyrione-Na and pyrione disulphide, phenols and phenol derivatives such as o-phenylphenol and p-chloro-m-cresol, aromatic alcohols or derivatives of aromatic alcohols, such as phenoxyethanol and phenoxypropanols, isothiazolones such as 1,2-benzisothiazolone, n-butyl-benzisothiazolone, octylisothiazolone, cyclohexylhydro-xydiazene 1-oxide and derivatives such as cyclohexyl-hydroxydiazene 1-oxide K salt.

Preferred active ingredients here are pyrione-sodium, O-phenylphenol, phenoxyethanol, 1,2-benzisothiazolone and octylisothiazolone, and cyclohexylhydroxydiazene 1-oxide K salt.

Particular preference is given to pyrithione compounds and in particular pyrione-Na.

The use amount in the concentrate can in each case be in the range from 0.1 to 5% by weight, preferably 0.2 to 2% by weight, more preferably 0.3 to 1% by weight, in particular 0.4 to 0.8% by weight.

(iv) Glycol

Glycols used according to the invention are preferably monoethylene glycol, butyl diglycol and 1,2-propylene glycol. It is preferred that the total amount of glycol is 5 to 60% by weight, preferably 10 to 50% by weight, more preferably 20 to 40% by weight, such as, for example, 25 to 30% by weight.

In the case of a content of 1,2-propylene glycol, this is preferably present in an amount of from 2 to 50% by weight, more preferably 5 to 20% by weight, in particular 10 to 30% by weight, such as 15 to 25% by weight, for example about 20% by weight.

In the case of a content of butyl diglycol in the concentrate according to the invention, this is preferably present in an amount of from 2 to 50% by weight, more preferably 2 to 20% by weight, in particular 3 to 15% by weight, such as 4 to 10% by weight, for example about 7% by weight.

Concentrates according to the invention are characterized in that they are comparatively low-odour. Accordingly, it is not necessary according to the present invention to make the odour acceptable through the water content being high. Concentrates according to the invention are thus characterized in that they comprise at most 10% by weight of water, such as at most 5% by weight, more preferably at most 3% by weight and in particular at most 2% by weight, with a maximum amount of 1% by weight being particularly preferred.

According to the invention, concentrates are provided in which a large number of active ingredients is not necessarily present. Accordingly, preferred concentrates according to the invention are characterized in that they are free from active ingredients of classes (a) isothiazolone, (b) benzimidazole compound, in particular 1H-benzimidazol-2-ylcarbamic acid derivative, (c) iodopropynyl compound, in particular iodopropynyl butylcarbamate, (d) iodoacetamide and/or (e) thiophene compound.

Moreover, the invention relates to the use of the mentioned concentrate for the cleaning and disinfection of installations in the metal working industry. For use, the concentrate is used in an amount of preferably 0.1 to 5% by weight, based on the dilute aqueous solution, preferably 0.2 to 1% by weight, such as, for example, 0.5% by weight. Such dilute aqueous solutions are adequately effective against a large number of germs, such as *E. coli, C. albicans, R. mucilagninosa, P. aeruginosa, K. pneumoniae* and *F. oxysporum*.

The advantages of the present invention arise in particular from the following examples. Unless expressly stated otherwise, amounts are given in % by weight.

EXAMPLES

Method For Determining the Formaldehyde Content

1. Principle:

The formaldehyde to be determined is driven out of the matrices under investigation by means of steam distillation. The steam/formaldehyde mixture is passed over a distillation bridge and condenses in an intensive condenser. The condensate is collected in a measuring flask. An aliquot fraction of this water/formaldehyde mixture is reacted. The formaldehyde condenses with 2,4-pentanedione in the presence of ammonium salts to give the 3,5-diacetyl-1,4-dihydrolutedine. The resulting 3,5-diacetyl-1,4-dihydrolutedine is intense yellow in colour, which can be quantified photometrically.

2. Procedure:

The size of the initial weight is governed by the formaldehyde content to be expected in the sample. In the subsequent steam distillation, distillation is carried out to a volume of 100 ml (or 250 ml). The formaldehyde content in the distillate should be 0.10 mg/l to 0.2 mg/l, so that 5 to 20 ml of the distillate can be used for the reaction. In the case of water-soluble samples with a relatively high formaldehyde content (no direct distillation possible), an appropriate initial weight is weighed into a 100 ml measuring flask and topped up with demineralized (dem.) water. 5 to 10 ml of this solution are used for the reaction. In the case of water-insoluble samples, the initial weight is rinsed over into the Antona insert with dem. water, or it is weighed directly into the insert.

The sample to be distilled is admixed with 10 ml of 20% sulphuric acid (depending on the objective, a neutral or alkaline distillation is also possible). To check for quantitative distillation, after the intended volume has been distilled off, additionally about 1 ml of distillate and 1 ml of formaldehyde reagent can be tested in a test tube with heating for a formaldehyde reaction.

From the distillate (100 ml or 250 ml), 2 to 20 ml are placed in a 25 ml measuring flask and admixed with 5 ml of formaldehyde reagent and topped up to 25 ml with dem. water. The flask is placed in a water batch at 40° C. for 30 minutes. After cooling to room temperature, the absorbance of the solution is measured in 1 cm glass cells in a UV photometer at 412 nm against a blank sample (blank sample: 5 ml of formaldehyde reagent are topped up to 25 ml with dem. water and also heated for 30 minutes at 40° C.).

3. Evaluation:

Quantitative evaluation of the formaldehyde samples takes place against a formaldehyde calibration curve in a UV photometer. The calibration curve is created by means of appropriate initial weights and dilution of the 37% formaldehyde solution, with steam distillation not being necessary. The solutions for the calibration curve are placed into 25 ml measuring flasks, admixed with 5 ml of formaldehyde reagent and topped up with dem. water. The flasks are placed in a water bath at 40° C. for 30 minutes and, after cooling to room temperature, measured against a blank sample at 412 nm.

Example 1

The following example concentrates 1A to 1I and 2 according to the invention were formulated for various periods at different temperatures. Example 1J is not in accordance with the invention. The change in the content of cleavable formaldehyde and pyrione-sodium, the change in the colour number according to Hazen and the change in the pH of a 1% strength by weight solution of the concentrates in demineralized water were investigated. The results are shown in the tables below. The following abbreviations apply here:

| Abbreviation | Meaning |
| --- | --- |
| Colour number | Colour number according to Harzen (unless stated otherwise) |
| pH | pH of a 1% strength by weight solution in demineralized water (unless stated otherwise) |
| Soln. | Solution |
| L | Lawn-like growth |
| + | Slight growth |

| Abbreviation | Meaning |
|---|---|
| ++ | Moderate growth |
| +++ | Considerable growth |
| ++++ | Massive growth |
| − | Growth-free |

The formaldehyde donor compound X comprises a mixture of formaldehyde donor compound and pyrione-sodium. The product is prepared from amine and paraformaldehyde by condensation and subsequent addition of monoethylene glycol, urea and pyrione-Na, followed by removal of water. This produces a mixture which comprises 3,3'-methylenebis(5-methyloxazolidine) as formaldehyde donor compound, urea, monoethylene glycol and pyrione-sodium.

| | 1A | 1B | 1C | 1D | 1E |
|---|---|---|---|---|---|
| Plurafac LF 224 | 10.0% | 10.0% | | 20.0% | |
| Plurafac LF 120 | 10.0% | | 10.0% | | 20.0% |
| Lutensol ON 70 | | 10.0% | 10.0% | | |
| Triethanolamine | 3.0% | 3.0% | 3.0% | 3.0% | 3.0% |
| Butyl diglycol | 7.0% | 7.0% | 7.0% | 7.0% | 7.0% |
| X | 50.0% | 50.0% | 50.0% | 50.0% | 50.0% |
| Propylene glycol | 20.0% | 20.0% | 20.0% | 20.0% | 20.0% |
| Water | | | | | |
| Appearance | Clear, pale yellow soln. | Clear, pale yellow soln. | Clear, pale yellow soln. | Clear, pale yellow soln. | Clear, pale yellow soln. |
| Colour number | 102 | 81 | 83 | 61 | 85 |
| pH | 10.4 | 10.4 | 10.3 | 10.4 | 10.3 |
| Content of HCHO after 11 days | 19.8% | 19.9% | 19.9% | 19.8% | 19.7% |
| Content of Na-pyrione after 8 days | 0.57% | 0.58% | 0.57% | 0.58% | 0.56% |
| After storage for 5 weeks at 25° C. | | | | | |
| Appearance | Clear, pale yellow soln. | Clear, pale yellow soln. | Clear, pale yellow soln. | Clear, pale yellow soln. | Clear, pale yellow soln. |
| Colour number | 122 | 114 | 136 | 115 | 147 |
| After storage for 5 weeks at 40° C. | | | | | |
| Appearance | Clear, yellow soln. | Clear, yellow soln. | Clear, yellow soln. | Clear, pale yellow soln. | Clear, yellow soln. |
| Colour number | 425 | 316 | 569 | 139 | 622 |
| After storage for 6 weeks at 40° C. | | | | | |
| Content of HCHO | 19.8% | 19.6% | 19.6% | 19.7% | 19.4% |
| After storage for 7 months at 25° C. | | | | | |
| Appearance | Clear, pale yellow soln. | Clear, pale yellow soln. | Clear, pale yellow soln. | Clear, pale yellow soln. | Clear, yellow soln. |
| Colour number | 158 | 139 | 202 | 131 | 271 |
| Content of Na-pyrione | 0.52% | 0.54% | 0.50% | 0.55% | 0.48% |
| Content of HCHO | 19.6% | 19.8% | 19.8% | 19.8% | 19.7% |
| After storage for 7 months at 40° C. | | | | | |
| Appearance | Clear, yellow soln. | Clear, pale yellow soln. | Clear, orange-yellow soln. | Clear, yellow soln. | Clear, orange-yellow soln. |
| Colour number (according to Gardner) | 5.4 | 4.7 | 6.1 | 3.6 | 6.4 |
| Content of Na-pyrione | 0.50% | 0.50% | 0.51% | 0.52% | 0.51% |
| Content of HCHO | 19.1% | 19.4% | 19.0% | 19.4% | 19.0% |

| | 1F | 1G | 1H | 1I | 1J (Comparison) |
|---|---|---|---|---|---|
| Plurafac LF 224 | | 5.0% | 15.0% | 7.0% | 10.0% |
| Plurafac LF 120 | | 15.0% | 5.0% | 7.0% | 10.0% |
| Lutensol ON 70 | 20.0% | | | 7.0% | |
| Triethanolamine | 3.0% | 3.0% | 3.0% | 3.0% | 3.0% |
| Butyl diglycol | 7.0% | 7.0% | 7.0% | 7.0% | 7.0% |
| X | 50.0% | 50.0% | 50.0% | 50.0% | 50.0% |
| Propylene glycol | 20.0% | 20.0% | 20.0% | 19.0% | |
| Water | | | | | 20.0% |
| Appearance | Clear, pale yellow soln. | Clear, pale yellow soln. | Clear, pale yellow soln. | Clear, pale yellow soln. | Clear, pale yellow soln. |
| Colour number | 79 | 79 | 70 | 79 | 46 |
| pH | 10.4 | 10.3 | 10.4 | 10.4 | 10.4 |
| Content of HCHO after 11 days | 19.7% | 19.8% | 19.9% | 19.8% | 19.8% |
| Content of Na-pyrione after 8 days | 0.56% | 0.57% | 0.58% | 0.57% | 0.57% |
| After storage for 5 weeks at 25° C. | | | | | |
| Appearance | Clear, pale yellow soln. | Clear, pale yellow soln. | Clear, pale yellow soln. | Clear, pale yellow soln. | Clear, pale yellow soln. |
| Colour number | 112 | 124 | 111 | 124 | 115 |
| After storage for 5 weeks at 40° C. | | | | | |
| Appearance | Clear, yellow | Clear, yellow | Clear, yellow | Clear, pale | 2 phases, |

| | soln. 477 | soln. 570 | soln. 313 | yellow soln. 450 | orange 8.1 (Gardner lower phase) |
|---|---|---|---|---|---|
| Colour number | | | | | |
| After storage for 6 weeks at 40° C. | | | | | |
| Content of HCHO | 19.7% | 19.6% | 19.8% | 19.6% | 16.9% |
| After storage for 7 months at 25° C. | | | | | |
| Appearance | Clear, pale yellow soln. | Clear, pale yellow soln. | Clear, pale yellow soln. | Clear, pale yellow soln. | Opaque, yellow soln. |
| Colour number | 156 | 258 | 142 | 198 | |
| Content of Na-pyrione | 0.53% | 0.48% | 0.52% | 0.50% | 0.47% |
| Content of HCHO | 19.7% | 19.7% | 19.8% | 19.8% | 18.3% |
| After storage for 7 months at 40° C. | | | | | |
| Appearance | Clear, yellow soln. | Clear, orange-yellow soln. | Clear, yellow soln. | Clear, yellow soln. | |
| Colour number (according to Gardner) | 5.7 | 6.0 | 4.7 | 5.4 | |
| Content of Na-pyrione | 0.50% | 0.50% | 0.51% | 0.52% | 0.52% |
| Content of HCHO | 19.2% | 18.9% | 19.1% | 18.9% | 10.2% |

Example 2

| | |
|---|---|
| Plurafac LF 224 | 10.0% |
| Poly-EO-5 isotridecyl ether | 10.0% |
| Triethanolamine | 3.0% |
| Butyl diglycol | 7.0% |
| X | 50.0% |
| Propylene glycol | 19.0% |
| Bevaloid 581 B | 0.5% |
| 1H-Benzotriazole | 0.5% |
| Appearance | Clear, yellow soln. |
| After storage for 9 days | |
| Colour number | 130 |
| pH | 10.1 |
| pH (1% in town water) | 9.4 |
| Content of HCHO after 5 days | 20.1% |
| Content of pyrione-Na after 5 days | 0.59% |

| | Storage temperature | | | |
|---|---|---|---|---|
| | −5° C. | +4° C. | 25° C. | 40° C. |
| Content of HCHO after 1 month | | | 20.4% | 20.1% |
| Content of Na-pyrione after 1 month | | | 0.56% | 0.53% |
| After storage for 3 months at the stated temperature | | | | |
| Appearance | Cloudy, yellowish solution | Cloudy, yellowish solution | Clear, yellow solution | Clear, yellow solution |
| Appearance after heating to room temperature | Clear, yellow solution | Clear, yellow solution | Clear, yellow solution | Clear, yellow solution |
| Colour number | | | 147 | 603 |
| pH | | | 10.1 | 10.1 |
| Content of HCHO | | | 20.3% | 20.0% |
| Content of Na-pyrione | | | 0.56% | 0.51% |

Example 2 shows that concentrates according to the invention have excellent long-term stability, with the active ingredient content only decreasing very slowly, as is inferred in particular from the stability upon storage at elevated temperature. The concentrates of Examples 1A to 1I and Example 2 have a weak odour, with the formaldehyde odour being virtually undetectable. By contrast, Comparison Example 1J has a considerably stronger odour, with the formaldehyde odour being significantly detectable. Measurements with formaldehyde Drager tubes in the gas phase above the concentrates indicate only slight formaldehyde emissions into the gas phase of concentrates 1A to 1I. By contrast, Drager tubes in the gas phase above the commercial product Grotanol® SR 3 indicate high formaldehyde emissions.

Example 3

| Test method used (germ count reduction test) | |
|---|---|
| Solutions and nutrient media | CSA (casein peptone-soya flour peptone agar) |
| | CSL (casein peptone-soya flour peptone solution) |
| | SA (Sabouraud agar) |
| | NaCl (physiological sodium chloride solution, 0.85%) |
| Test germs | *Aspergillus niger* ATCC 6275 |
| | *Candida albicans* ATCC 10231 |
| | *Pseudomonas aeruginosa* ATCC 15442 |
| | *Pseudomonas fluorescens* ATCC 17397 |
| | *Pseudomonas putida* ATCC 12633 |
| | *Staphylococcus aureus* ATCC 6538 |

Cultivation and Preparation of the Inoculation Solutions

Bacteria 24-hour CSL cultures are made up from 24-hour CS slant agar cultures of *Staphylococcus aureus/Pseudomonas aeruginosa*. Incubation takes place at 37° C.

48-hour CSL cultures are made up from 48-hour CS slant agar cultures of *Pseudomonas fluorescens/Pseudornonas putida*.

The titre of the bacterial suspension is about $10^9$ CFU/ml.

Yeast

A 4-day old *Candica albicans* culture (CSA+dextrose) is suspended with 5 ml of physiological sodium chloride solution and adjusted according to a barium sulphate standard (see DVG guideline). The titre of the *Candica albicans* suspension is $10^8$ CFU/ml.

Fungi

A 7- to 14-day old *Aspergillus niger* culture on Sabouraud agar is suspended with 5 ml of NaCl, filtered through a glass filter containing glass wool and made up to 200 ml. This suspension has a titre of about $10^7$ CFU/ml.

Procedure

A dilution series of four concentrations is produced from the formulation to be tested and poured into sterile 10 ml tubes. One dilution series per test germ is required. Each tube is inoculated with 0.1 ml of the individual germ suspension.

After 6, 24, 48 and 168 hours, the samples are streaked onto CSA or Sabouraud agar using sterile glass rods. The bacteria are streaked onto CSA and incubated for 48 hours at 37° C. (*Pseudomonas aeruginose* and *Staphylococcus aureus*) or 25° C. (*Pseudomonas fluorescens/Pseudomonas putda*). The fungi are streaked onto Sabouraud agar and incubated for 48 hours at 37° C. (*Candida albicans*) and 25° C. (*Aspergillus niger*).

Results

| | | Germ count *E. coli* | | | |
|---|---|---|---|---|---|
| | Test material | 1 h | 3 h | 6 h | 24 h |
| A | Sterile town water | L | L | L | L |
| B | 1B 0.25% | +++ | − | − | − |
| C | 1B 0.5% | ++ | − | − | − |
| D | Grotanol ® SR 3 0.5% | ++++ | ++++ | ++++ | − |
| E | Grotanol ® SR 3 1.0% | ++++ | +++ | ++ | − |

| | | Germ count *C. albicans* | | | |
|---|---|---|---|---|---|
| | Test material | 1 h | 3 h | 6 h | 24 h |
| A | Sterile town water | L | L | L | L |
| B | 1B 0.25% | +++ | + | − | − |
| C | 1B 0.5% | − | − | − | − |
| D | Grotanol ® SR 3 0.5% | +++ | + | +(1) | − |
| E | Grotanol ® SR 3 1.0% | + | − | − | − |

| | | Germ count *R. mucilagninosa* | | | |
|---|---|---|---|---|---|
| | Test material | 1 h | 3 h | 6 h | 24 h |
| A | Sterile town water | L | L | L | L |
| B | 1B 0.25% | − | − | − | − |
| C | 1B 0.5% | − | − | − | − |
| D | Grotanol ® SR 3 0.5% | ++ | − | − | − |
| E | Grotanol ® SR 3 1.0% | + | − | − | − |

| | | Germ count *P. aeruginosa* | | | |
|---|---|---|---|---|---|
| | Test material | 1 h | 3 h | 6 h | 24 h |
| A | Sterile town water | L | L | L | L |
| B | 1B 0.25% | ++++ | − | − | − |
| C | 1B 0.5% | − | − | − | − |
| D | Grotanol ® SR 3 0.5% | ++++ | +++ | − | − |
| E | Grotanol ® SR 3 1.0% | +++ | − | − | − |

| | | Germ count *K. pneumoniae* | | | |
|---|---|---|---|---|---|
| | Test material | 1 h | 3 h | 6 h | 24 h |
| A | Sterile town water | L | L | L | L |
| B | 1B 0.25% | +++ | − | − | − |
| C | 1B 0.5% | − | − | − | − |
| D | Grotanol ® SR 3 0.5% | ++++ | +++ | + | − |
| E | Grotanol ® SR 3 1.0% | +++ | − | − | − |

| | | Germ count *F. oxysporum* | | | |
|---|---|---|---|---|---|
| | Test material | 1 h | 3 h | 6 h | 24 h |
| A | Sterile town water | L | L | L | L |
| B | 1B 0.25% | L | − | − | − |
| C | 1B 0.5% | + | − | − | − |
| D | Grotanol ® SR 3 0.5% | L | L | +(1) | − |
| E | Grotanol ® SR 3 1.0% | +++ | + | − | − |

Result:

Even at a low concentration, formulation 1B is considerably more effective than the commercial product Grotanol® SR 3.

The invention claimed is:

1. A concentrate for cleaning and disinfecting, comprising:
   (i) one or more alkyl alcohol alkoxylates,
   (ii) 3,3'-methylenebis (5-methyl oxazolidine),
   (iii) pyrione sodium,
   (iv) one or more glycols, and
   (v) optionally up to 10% by weight of water, wherein the concentrate is free from active ingredients of the following classes of compounds: (a) isothiazolone compound, (b) benzimidazole compound, (c) iodopropynyl compound and (d) iodoacetamide and/or thiophene compound.

2. The concentrate according to claim 1, wherein the alkyl alcohol alkoxylate is derived from linear or branched aliphatic alcohol having 6 to 18 carbon atoms and alkoxylated with up to 20 ethylene oxide, propylene oxide and/or butylene oxide groups.

3. The concentrate according to claim 2, wherein the alkyl alcohol alkoxylate is selected from the group consisting of: (a) isodecyl alcohol-7 ethylene oxide, (b) aliphatic $C_{12}$- to $C_{18}$-alcohol ethylene oxide/butylene oxide and (c) aliphatic $C_8$- to $C_{14}$-alcohol ethylene oxide/butylene oxide.

4. The concentrate according to claim 1, wherein component (i) is present in an amount of from 2 to 50% by weight.

5. The concentrate according to claim 1, wherein 3,3'-methylenebis (5-methyl oxazolidine) is present in an amount such that a fraction of formaldehyde which can be cleaved off the 3,3'-methylenebis is in a range of from 2 to 50% by weight.

6. The concentrate according to claim 1, wherein the pyrione sodium is present in an amount of from 0.1 to 5% by weight.

7. The concentrate according to claim 1, wherein the one or more glycol is selected from the group consisting of monoethylene glycol, butyl diglycol and 1,2-propylene glycol.

8. The concentrate according to claim 1, comprising 1,2-propylene glycol in an amount of from 2 to 50% by weight.

9. The concentrate according to claim 1, comprising butyl diglycol in an amount of from 2 to 50% by weight.

10. The concentrate according to claim 1, comprising water in a maximum amount of 1% by weight.

11. The concentrate according to claim 1, wherein component (i) is present in an amount of from 15 to 25% by weight.

12. The concentrate according to claim 1, wherein the 3,3'-methylenebis (5-methyl oxazolidine) is present in an amount such that a fraction of formaldehyde which can be cleaved off the 3,3'-methylenebis is in a range of from 15 to 25% by weight.

13. The concentrate according to claim 1, wherein the pyrione sodium is present in an amount of from 0.4 to 0.8% by weight.

14. The concentrate according to claim 1, comprising 1,2-propylene glycol in an amount of from 15 to 25% by weight.

15. The concentrate according to claim 1, comprising butyl diglycol in an amount of from 4 to 10% by weight.

16. The concentrate according to claim 1, comprising at most 5% by weight of water.

17. The concentrate according to claim 1, wherein the concentrate comprises 0% by weight of water.

* * * * *